United States Patent
Furey et al.

(10) Patent No.: US 7,921,740 B2
(45) Date of Patent: Apr. 12, 2011

(54) DISPOSABLE, PRE-STERILIZED FLUID RECEPTACLE SAMPLING DEVICE

(75) Inventors: James F. Furey, Brookline, MA (US); Stephen P. Proulx, Boxboro, MA (US)

(73) Assignee: Millipore Corporation, Billerica, MA (US)

( * ) Notice: Subject to any disclaimer, the term of this patent is extended or adjusted under 35 U.S.C. 154(b) by 70 days.

(21) Appl. No.: 11/878,126

(22) Filed: Jul. 20, 2007

(65) Prior Publication Data
US 2008/0022785 A1 Jan. 31, 2008

Related U.S. Application Data

(60) Continuation of application No. 11/415,264, filed on May 1, 2006, now Pat. No. 7,293,475, which is a division of application No. 10/746,030, filed on Dec. 23, 2003, now Pat. No. 7,293,477.

(51) Int. Cl.
*G01N 1/00* (2006.01)
(52) U.S. Cl. .................................. 73/863.86
(58) Field of Classification Search ................ None
See application file for complete search history.

(56) References Cited

U.S. PATENT DOCUMENTS

| | | | |
|---|---|---|---|
| 0,214,367 A | 4/1879 | Colvin | |
| 0,988,378 A | 4/1911 | Olson | |
| 1,831,457 A | 11/1931 | Larsen | |
| 1,852,445 A * | 4/1932 | Calkins et al. | 73/863.71 |
| 2,240,888 A * | 5/1941 | Hageline | 73/863.33 |
| 2,426,808 A | 12/1943 | Auer | |
| 2,712,881 A | 5/1951 | Mathisen | |
| 2,642,256 A | 6/1953 | Stehlin | |
| 2,736,201 A | 2/1956 | Ohlsen et al. | |
| 2,844,964 A | 7/1958 | Guibert | |
| 2,859,932 A | 11/1958 | Mackal | |
| 2,865,394 A | 12/1958 | Presley | |
| 3,038,485 A | 7/1961 | Hosek | |
| 3,039,482 A | 6/1962 | Goldberg | |
| 3,219,047 A | 6/1962 | Kircher, III et al. | |
| 3,390,677 A | 7/1965 | Razimbaud | |

(Continued)

FOREIGN PATENT DOCUMENTS
DE 8812723 U1 12/1988

(Continued)

OTHER PUBLICATIONS

Lynx Trademark Registration 2,831,931 dated Apr. 13, 2004.

(Continued)

*Primary Examiner* — Robert R Raevis
(74) *Attorney, Agent, or Firm* — Nields, Lemack & Frame, LLC

(57) ABSTRACT

The present invention provides a fluid sampling device comprising a port insert, a plurality of flexible conduits, and a plurality of sample containers. The port insert comprises a body having a plurality of shafts therethrough and a rotatably displaceable member for individually opening and closing any of said shafts to enable the flow of fluid therethrough. Flexible conduits (e.g., flexible tubing) are equal in number to the shafts, with each flexible conduit connected to or otherwise in fluid communication with an individual shaft. Similarly, sample containers (e.g., flexible bags) are equal in number to the conduits, with each sample container connected to an individual conduit opposite the connection to the shaft. A specific configuration for the port insert, as well as kit containing sterilized components of the fluid sampling device, are also described.

32 Claims, 7 Drawing Sheets

U.S. PATENT DOCUMENTS

| | | | |
|---|---|---|---|
| 3,223,100 A | | 12/1965 | Koenig et al. |
| 3,319,622 A | | 5/1967 | Shiner |
| 3,424,181 A | | 1/1969 | Morse |
| 3,479,880 A | * | 11/1969 | Mutter et al. ............... 73/863.73 |
| 3,525,350 A | | 8/1970 | Hosek |
| 3,633,621 A | * | 1/1972 | Myers ....................... 137/625.11 |
| 3,638,499 A | | 2/1972 | Saint-Andre |
| 3,678,959 A | | 7/1972 | Liposky |
| 3,747,411 A | | 7/1973 | McDermott |
| 3,779,082 A | | 12/1973 | Galloway |
| 3,802,782 A | * | 4/1974 | Natelson ....................... 356/409 |
| 3,848,581 A | | 11/1974 | Cinqualbre et al. |
| 3,858,449 A | | 1/1975 | Singer |
| 3,921,456 A | | 11/1975 | Newcomb, Jr. et al. |
| 4,064,003 A | | 12/1977 | Newton |
| 4,207,922 A | | 6/1980 | Andrieux et al. |
| 4,294,247 A | | 10/1981 | Carter et al. |
| 4,353,386 A | * | 10/1982 | Slagel ....................... 137/119.03 |
| 4,423,641 A | | 1/1984 | Ottung |
| 4,454,772 A | | 6/1984 | Brunner et al. |
| 4,479,393 A | | 10/1984 | Shores |
| 4,569,236 A | | 2/1986 | Kitchen et al. |
| 4,580,452 A | | 4/1986 | Masson |
| 4,584,887 A | | 4/1986 | Galen |
| 4,587,856 A | | 5/1986 | Otis |
| 4,587,887 A | | 5/1986 | Shibayama et al. |
| 4,630,847 A | | 12/1986 | Blenkush |
| 4,669,321 A | | 6/1987 | Meyer |
| 4,704,910 A | | 11/1987 | Conrad |
| 4,838,877 A | | 6/1989 | Massau |
| 4,942,901 A | | 7/1990 | Vescovini |
| 4,997,108 A | | 3/1991 | Hata |
| 5,058,619 A | | 10/1991 | Zheng |
| 5,095,765 A | | 3/1992 | Filbey et al. |
| 5,161,417 A | | 11/1992 | Strong et al. |
| 5,246,204 A | | 9/1993 | Ottung |
| 5,296,197 A | | 3/1994 | Newberg et al. |
| 5,360,413 A | | 11/1994 | Leason et al. |
| 5,375,477 A | | 12/1994 | Neill et al. |
| 5,398,557 A | | 3/1995 | Shimizu et al. |
| 5,452,746 A | | 9/1995 | Hoobyar et al. |
| 5,525,301 A | | 6/1996 | Newberg et al. |
| 5,542,305 A | * | 8/1996 | Hollinger .................... 73/863.73 |
| 5,730,418 A | | 3/1998 | Feith et al. |
| 5,747,708 A | | 5/1998 | Weiberth |
| 5,755,155 A | | 5/1998 | Buesing |
| 5,786,209 A | | 7/1998 | Newberg |
| 5,820,614 A | | 10/1998 | Erskine et al. |
| 5,829,425 A | | 11/1998 | Woods et al. |
| 5,911,252 A | | 6/1999 | Cassel |
| 5,948,998 A | | 9/1999 | Witte et al. |
| 6,009,684 A | | 1/2000 | Buesing |
| 6,030,578 A | | 2/2000 | McDonald |
| 6,032,543 A | | 3/2000 | Arthun et al. |
| 6,096,011 A | | 8/2000 | Trombley, III et al. |
| 6,133,022 A | | 10/2000 | Newberg |
| 6,162,206 A | | 12/2000 | Bindokas et al. |
| 6,170,800 B1 | | 1/2001 | Meloul et al. |
| 6,210,372 B1 | | 4/2001 | Tessmann et al. |
| 6,306,191 B1 | | 10/2001 | McInerney et al. |
| 6,314,987 B1 | | 11/2001 | Hay |
| 6,345,640 B1 | | 2/2002 | Newberg |
| 6,345,645 B1 | * | 2/2002 | Kenna et al. ............... 137/625.11 |
| 6,354,466 B1 | | 3/2002 | Karpisek |
| 6,386,137 B1 | | 5/2002 | Riche |
| 6,390,127 B2 | * | 5/2002 | Schick ....................... 137/625.11 |
| 6,477,906 B1 | | 11/2002 | Peterson |
| 6,516,677 B1 | | 2/2003 | Suter |
| 6,779,575 B1 | | 8/2004 | Arthun |
| 6,860,162 B1 | | 3/2005 | Jaeger |
| 6,871,669 B2 | | 3/2005 | Meyer et al. |
| 7,293,475 B2 | * | 11/2007 | Furey et al. ................. 73/863.31 |
| 7,350,535 B2 | | 4/2008 | Liepold et al. |
| 7,578,205 B2 | | 8/2009 | Belongia |
| 2002/0129858 A1 | | 9/2002 | Meyer et al. |
| 2003/0188588 A1 | | 10/2003 | Jaeger |
| 2005/0016620 A1 | | 1/2005 | Proulx et al. |
| 2005/0132821 A1 | | 6/2005 | Furey et al. |
| 2006/0142730 A1 | | 6/2006 | Proulx et al. |
| 2006/0201263 A1 | | 9/2006 | Furey et al. |
| 2007/0106264 A1 | | 5/2007 | Proulx et al. |
| 2008/0022785 A1 | | 1/2008 | Furey et al. |
| 2009/0019952 A1 | | 1/2009 | Furey et al. |

FOREIGN PATENT DOCUMENTS

| | | | |
|---|---|---|---|
| DE | 100 39 196 A | | 2/2002 |
| DE | 603 10 700 | | 10/2007 |
| EP | 0107579 A2 | | 5/1984 |
| EP | 0154002 B1 | | 9/1985 |
| EP | 0508749 A2 | | 10/1992 |
| EP | 0 468 957 B1 | | 6/1994 |
| EP | 0 684 050 | | 11/1995 |
| EP | 1008359 A1 | | 6/2000 |
| EP | 1 499 382 | | 11/2003 |
| EP | 1 548 420 | | 6/2005 |
| EP | 1 962 076 A2 | | 8/2008 |
| GB | 1 573 482 | | 8/1980 |
| GB | 2 327 369 A | | 1/1999 |
| GB | 2 365 511 | | 2/2002 |
| JP | 58-131802 | | 9/1983 |
| JP | 2-052667 A | | 2/1990 |
| JP | 02-118276 | | 5/1990 |
| JP | 6-023045 A | | 2/1994 |
| JP | 06-327772 | | 11/1994 |
| JP | 07-051371 | | 2/1995 |
| JP | 08-168535 | | 7/1996 |
| JP | 9-154945 A | | 6/1997 |
| JP | 11-141713 | | 5/1999 |
| JP | 11-270705 | | 10/1999 |
| JP | 2000-55792 | | 2/2000 |
| JP | 2001-170188 A | | 6/2001 |
| JP | 2001-269401 | * | 10/2001 |
| JP | 4332106 | | 7/2005 |
| JP | 2008-185218 | | 8/2008 |
| JP | 20092965 | | 1/2009 |
| JP | 2009192540 | | 8/2009 |
| WO | 9012972 | | 11/1990 |
| WO | 9408173 | | 4/1994 |
| WO | 9630076 | | 10/1996 |
| WO | WO 97/16715 | | 5/1997 |
| WO | 9845188 | | 10/1998 |
| WO | 9850105 | | 11/1998 |
| WO | 9903568 | | 1/1999 |
| WO | 99/06089 A1 | | 2/1999 |
| WO | 00/78472 A1 | | 12/2000 |
| WO | WO-03/090843 | | 11/2003 |
| WO | WO 03090842 A1 | | 11/2003 |

OTHER PUBLICATIONS

Wendt, D., "Disposable processing systems; how suppliers are meeting today's biotech challenges from fluid handling to filtration", Biopharm Internation, p. 18 (Jul. 1, 2003).

About Fluid Line Technology, http://www/fluidlinetech.com/aboutus.html dated Oct. 30, 2009.

Allegro Single-use Systems—Recommended Capsule Filters and Membranes, http://www.pall.com/variants/print/biopharm_48022.asp dated Oct. 30, 2009.

Microbiological Analysis, Sampling Ports, 1989, p. 130.

NovaSeptum, NovAseptic, Feb. 2003, "NovaSeptum Liquid Sampling System", 4-Pages.

Process Worldwide-PharmaTEC Jun. 2004; "Bridging the gap A case study in the validation of hybrid connectors"; 3-Pages.

Office Action dated Mar. 19, 2010 in a corresponding application (U.S. Appl. No. 12/284,666).

Office Actions dated Sep. 22, 2005, Apr. 12, 2006, Nov. 16, 2006, Sep. 10, 2007, Apr. 15, 2008, Nov. 28, 2008, Apr. 14, 2009; Notice of Allowances dated Jan. 25, 2010, Apr. 15, 2010 and Aug. 12, 2010 in co-pending U.S. Appl. No. 10/500,077.

Office Actions dated Aug. 19, 2009 and May 12, 2010 in co-pending U.S. Appl. No. 11/350,384.

Office Action dated Mar. 16, 2010 in co-pending U.S. Appl. No. 11/584,301.

Office Action dated Mar. 19, 2010 in corresponding U.S. Appl. No. 12/284,666.

Memorandum and Order, Document No. 70, dated Sep. 20, 2010, in the United States District Court for the District of Massachusetts, Civil Action No. 09-10765-DPW.

Japanese communication dated Jul. 27, 2010 in co-pending foreign application (JP2008-070904).

Office Action dated Oct. 7, 2010 in co-pending U.S. Appl. No. 11/584,301.

Notice of Allowance and Supplemental Notice of Allowances dated Oct. 1, 2010, Oct. 7, 2010, Oct. 15, 2010 and Oct. 20, 2010 in co-pending U.S. Appl. No. 12/284,666.

European communication dated Oct. 29, 2010 in a co-pending foreign application (EP10179151.5).

European communication dated Oct. 29, 2010 in a co-pending foreign application (EP10179183.8).

Indian communication dated Oct. 18, 2010 in a co-pending foreign application (IN1444/DELNP/2004).

Notice of Allowance dated Dec. 7, 2010 in a co-pending U.S. Appl. No. 10/500,077.

Notice of Rejection with English Translation, JP2003-587467, Jul. 24, 2007.

International Search Report for PCT/US03/12927 dated Aug. 6, 2003.

International Preliminary Examination Report for PCT/US03/12927 dated Feb. 11, 2004.

International Search Report for PCT/US03/13073 dated Aug. 6, 2003.

European Search Report EP 1548420 A3, dated Mar. 13, 2006.

International Search Report for PCT/US03/12924, dated Aug. 6, 2003.

Gore's Preliminary Invalidity Contentions to Plaintiff Millipore Corporation, Document No. 21, filed Oct. 29, 2009 in the United States District Court for the District of Massachusetts, Civil Action No. 09-10765 DPN.

Janetchek, R., "Capsule Filters & Disposable Sterile Processing Systems", Pharmaceutical Processing, p. 8 (Jan. 2001).

Charter Medical, Ltd., Bioprocess Products, "New Quality of Data for Bioprocessings Bags", Pharmaceutical Processing, p. 8 (Jan. 2002).

Greene, R., et al., "Disposable Equipment: A Mainstay in Bioprocessing", Chemical Engineering Progress, pp. 10-11 (Nov. 2002).

Haughney, H., et al., "Taking Disposable Processing to the Next Level", Biopharm Trends, pp. 20-22 (Jun. 2004).

Tingley, S., "Plastic factory: Disposable biopharmaceutical manufacturing takes a giant leap forward", Alternative Manufacturing, pp. S4-S9 (Feb. 2003).

Tingley, S., "Plastic factory, Part II: The final pieces of the disposable puzzle", Alternative Manufacturing, pp. 12-14 (Jun. 2003).

Aranha, H. et al., "Disposable processing gains you a competitive edge: enhancing manufacturing capacity with disposable filters, connectors, and membrane chromatography", Biopharm International, p. 50 (Oct. 2003).

Millipore's Initial Infringement Contentions, Document No. 19, filed Oct. 8, 2009 in the United States District Court for the District of Massachusetts, Civil Action No. 09-10765 DPW.

Gore's Preliminary Non-Infringement contentions to Plaintiff Millipore Corporation, Document No. 20, filed Oct. 29, 2009 in the United States District Court for the District of Massachusetts, Civil Action No. 09-10765 DPW.

Lynx ST Connectors http://www.millipore.com/catalogue/module/c9131 dated Oct. 30, 2009.

Pure-Flo Hygienic diaphragm valves, actuators, and switch packages, http://www.ittpureflo.com/valvetype.html dated Oct. 30, 2009.

Valves, Gemu Valves and Distrivutor, Diaphragm Valves, Sanitary Valves, Aseptic Valves, Valves and Fittings, http://www.casellasales.com, dated Oct. 30, 2009.

Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009.

International Preliminary Examination Report for PCT/US03/12924 dated Jul. 8, 2004.

NovAseptic—How to Use NA sampling system, http://www.novaseptic.se/main.as?typ=6 dated Feb. 13, 2002.

Steam-In-Place Bag Connector, http://www.fluidcomponents.net/tc_tech.html, download on Feb. 18, 2010.

Pharmenta AptiPort Sampling Valve, http://www.web.archive.org/web/20031029084907/http://www.pharmenta.com/aptiport.htm, dated Feb. 18, 2010.

Daily Business Briefing—"Entegris Introduces the First ALL TEFLON PFA" dated Apr. 16, 2002.

Block, S.S. "Disinfection, Sterilization, and Preservation (Fourth Edition)", Lea & Febiger, ISBN:0-8121-1364-0 (1991).

* cited by examiner

DISPOSABLE, PRE-STERILIZED FLUID RECEPTACLE SAMPLING DEVICE

CROSS-REFERENCE TO RELATED APPLICATIONS

This application is a continuation patent application of U.S. application Ser. No. 11/415,264, filed on May 1, 2006, now U.S. Pat. No. 7,293,475 which is a divisional patent application of U.S. application Ser. No. 10/746,030, filed on Dec. 23, 2003, now U.S. Pat. No. 7,293,477 the entire contents of which are incorporated by reference herein.

FIELD

In general, the present invention is directed to a fluid sampling device, and in particular, to a fluid sampling device having a configuration amenable to "single-use disposability", while still enabling good aseptic sampling.

BACKGROUND

When conducting complex and/or delicate fluid processes within a "closed" fluid receptacle, to monitor the progress of the process, it is often desirable to withdraw and analyze samples of the fluid without disturbing the process, such as may occur upon "opening" the receptacle. For example, in the study and/or manufacture of biochemical products (e.g., biopharmaceuticals), biochemical fluid is often contained in an aseptically "closed" fermenting tank, bioreactor, or like fluid receptacle, wherein the fluid is processed over comparatively long periods of time, under diverse and changing chemical and environmental conditions. By withdrawing and analyzing samples of the fluid intermittently in the course of the process, one can learn more about the progress of the process, and if called for, take prophylactic measures to change the outcome thereof.

Similar issues arise also in instances wherein fluid is conducted through a conduit, or a pipe, or other like fluid receptacle. Sampling of said fluid is often difficult because in many industrial systems, said receptacles are not easily opened or disassembled to allow one to withdraw fluid samples, especially in a sterile manner.

While several fluid sampling techniques are known, certain technical issues can be noted. For example, certain integrated fluid sampling fixtures comprise stainless steel valves and piping which, for biopharmaceutical applications, often require laborious steam sterilization and cleaning prior to use. (See e.g., U.S. Pat. No. 5,948,998, issued to L. D. Witte et al. on Sep. 7, 1999). Other fluid sampling devices are difficult to integrate into extant fluid processing systems, for example, by requiring the installation of custom-fitted ports onto a host fluid receptacle. (See e.g., U.S. Pat. No. 6,032,543, issued to Nils Arthun et al. on Mar. 7, 2000). Still other devices, although adapted for use in standard industrial ports, are complex and costly instruments comprising valves, inlets, outlets, seals, needles, and other components, all precisely arranged, but capable of only a single aseptic sample per sterilization cycle. (See e.g., U.S. Pat. No. 4,669,321, issued to Pio Meyer on Jun. 2, 1987). Finally, the majority of fluid sampling devices—as is the case in many of those already mentioned—require in their operation the piercing of a septum using a hypodermic needle. (See also, e.g., U.S. Pat. No. 4,423,641, issued to K. Ottung on January 1984; and U.S. Pat. No. 2,844,964, issued to F. W. Guibert on Jul. 29, 1958).

In light of the above, a need exists for a fluid sampling device that is sufficiently inexpensive in its construction to promote single-use disposability, capable of being used in standard industrial ports commonly found in fluid receptacles, and capable of several good sterile fluid sample withdrawals per sterilization cycle and/or prior to being exhausted.

SUMMARY

The present invention provides a fluid sampling device comprising a port insert, a plurality of flexible conduits, and a plurality of sample containers. The port insert comprises a body having a plurality of shafts therethrough, and sample grating means for individually opening and closing any of said shafts to control the flow of fluid therethrough. The sample gating means comprise single or multiple members that are displaceable between "open" and "closed" positions such that fluid can flow through said body through one of said shafts in said "open" position, but not in said "closed" position. Each shaft is in fluid communication with a flexible conduit, which in turn, is in fluid communication with a sample container. The sample containers are preferably flexible bags; and the conduits, preferably, flexible tubing.

In a principal embodiment, the port insert is configured as a monolithic body having a plurality of rigid elongate members disposed therethrough in a manner allowing linear displacement of said members between said "closed" and "open" positions. When the port insert is installed into a suitable port provided on a fluid receptacle, an elongate member can be moved into its "open" position, whereupon, fluid contained within the receptacle flows into the elongate member, then through the flexible conduit, and ultimately into the sample container. After the desired amount of fluid is collected in the sample container, the elongate member is moved and locked into its "closed" position, the flexible conduit is severed (preferably, aseptically), and the sample container taken for further analysis. The process can then be repeated, by using the remaining elongate members. When all elongate members are exhausted, the port insert is fully spent and can be easily removed and replaced after the fluid processes in the fluid receptacle are concluded.

In light of the above, it is a principal object of the present invention to provide a fluid sampling device.

It is another object of the present invention to provide a fluid sampling device that enables the withdrawal of several samples of fluid from a fluid receptacle.

It is another object of the present invention to provide a fluid sampling device that enables the withdrawal of several samples of fluids from a fluid receptacle, wherein said withdrawal occurs in a substantially sterile manner, and wherein inter-sample cross-contamination is substantially discouraged.

It is another object of the present invention to provide a fluid sampling device that enables the withdrawal of several samples of fluid from a fluid receptacle, the fluid sampling device capable of being configured to promote so-called "single-use disposability".

It is another object of the present invention to provide a fluid sampling device comprising a port insert, a plurality of flexible conduits, and a plurality of sample containers (preferably, flexible, bag-like sample containers).

It is another object of the present invention to provide a port insert useful for making a fluid sampling devices, said port insert maximizing functionality with a minimal number of comparatively inexpensive components, thus promoting said "single use disposability".

It is another object of the present invention to provide a kit containing in sterilized packaging the assembled, partially assembled, or unassembled components of a fluid sampling device, wherein all contained components are sterilized.

These and other objects of the present invention can be better understood in view of the detailed description herein, read in conjunction with the attached drawings.

DETAILED DESCRIPTION

Figure 1:
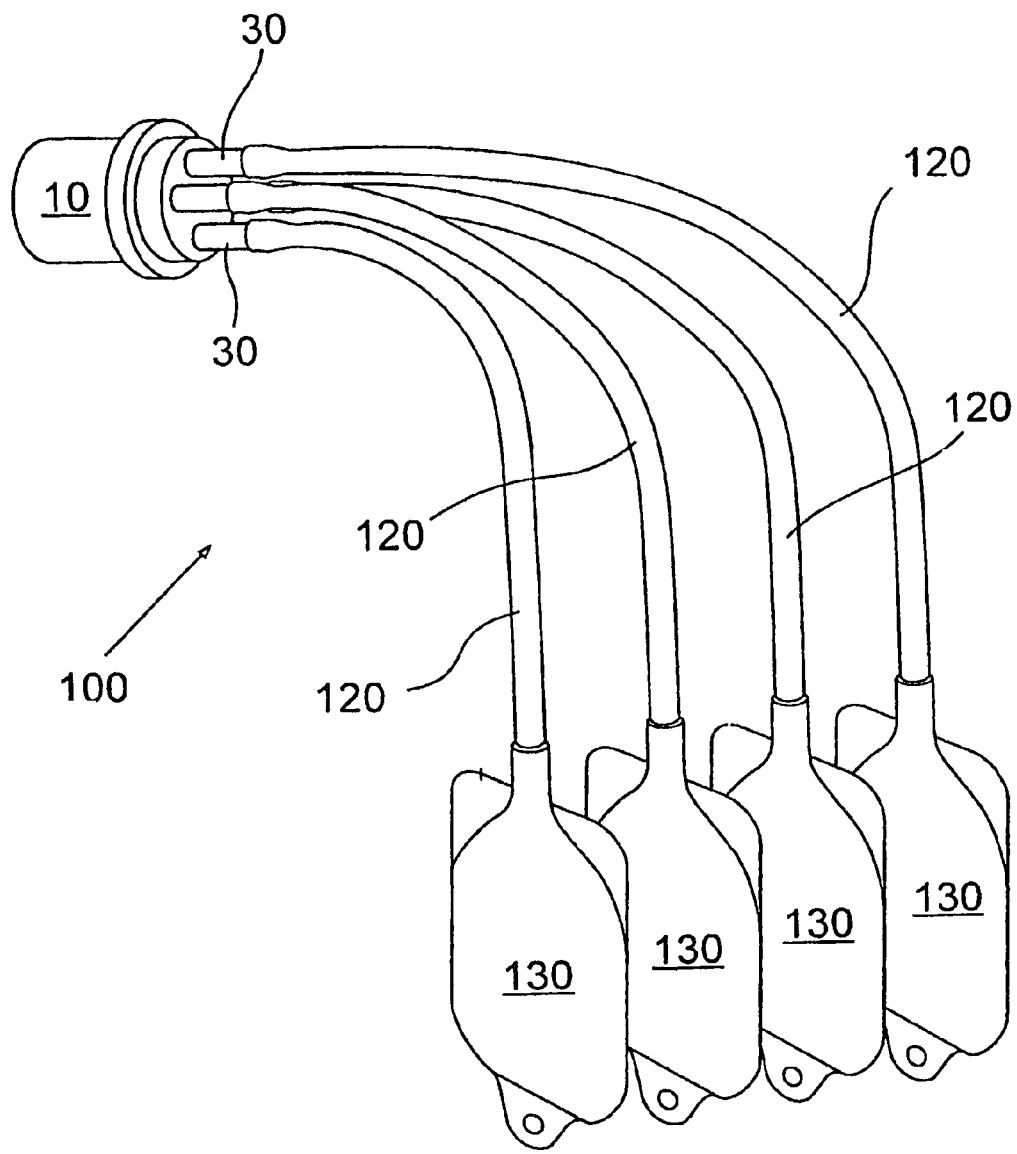
FIG. 1 schematically illustrates a fluid sampling device 100 according to an embodiment of the present invention, the fluid sampling device 100 comprising a port insert 10, a plurality of flexible conduits 120, and a plurality of sample containers 130.

As illustrated in FIG. 1, the fluid sampling device 100 of the present invention comprises, in general, a port insert 10, a plurality of flexible conduits 120, and a plurality of sample containers 130. When the port insert 10 is "plugged" into a host fluid receptacle (such as a bioreactor vessel or pipe), samples of fluid can be removed sequentially from the host fluid receptacle, and collected in individual sample containers, without substantially disturbing, corrupting, or otherwise affecting any ongoing fluid processes occurring within the host. Upon completion of said fluid processes, the spent (or partially spent) fluid sampling device 100 is removed, allowing comparatively easy replacement with a fresh unit prior to conducting another of said fluid processes.

The port insert 10 includes a plurality of shafts, each providing an avenue through which fluid can flow from the host fluid receptacle into one of said sample container 130. The port insert 10 further comprises sample gating means for individually opening and closing said shafts to control the flow of fluid therethrough. The sample gating means comprise single or multiple members displaceable between "open" and "closed" positions such that fluid can flow through said body through one of said shafts in said "open" position, but not in said "closed" position. Each individual elongate member is connected to (or otherwise in fluid communication with) a flexible conduit, which in turn, is connected to (or otherwise in fluid communication with) a sample container.

In operation, prior to being charged with fluid, a host fluid receptacle is cleaned, sterilized, and otherwise prepared for processing. The pre-sterilized fluid sampling device is installed into an existing port provided in the host and steam "sterilized-in-place". The fluid receptacle is then charged with the fluid, and fluid processing commences.

During the processing of the fluid, when a sample is desired for analysis, the sample gating means is displaced into an "open" position, whereupon fluid flows out of the host receptacle, through the active shaft, then through the attached fluid conduit, and ultimately into the sample container. After the desired quantity of fluid is collected, sample gating means is displaced into a "closed" position. The flexible conduit is then clamped off at two points, then severed between the two clamps, so that the captured sample can be removed for analysis. Preferably, a heat knife, flame, or the like, is used to both sever and seal the conduit simultaneously.

As the fluid process continues, if further samples are desired, another of the remaining unused shaft can be activated. This continues until all shafts are spent, or the fluid process ends. At the end of the fluid process, the fluid sampling device is removed, and disposed off in accordance with appropriate industrial practice. When the host receptacle is again needed for another processing operation, a fresh fluid sampling device is installed.

The fluid sampling device 100 is preferably made as a "single use" item. In this regard, it is "single use" in the sense that at the completion of the desired (or predetermined) number of fluid sampling operations, the device 100 can either be disposed (e.g., as is sometimes required by law after sampling certain environmentally-regulated substances) or partially recycled (e.g., after dispensing non-regulated substances).

Figure 2:
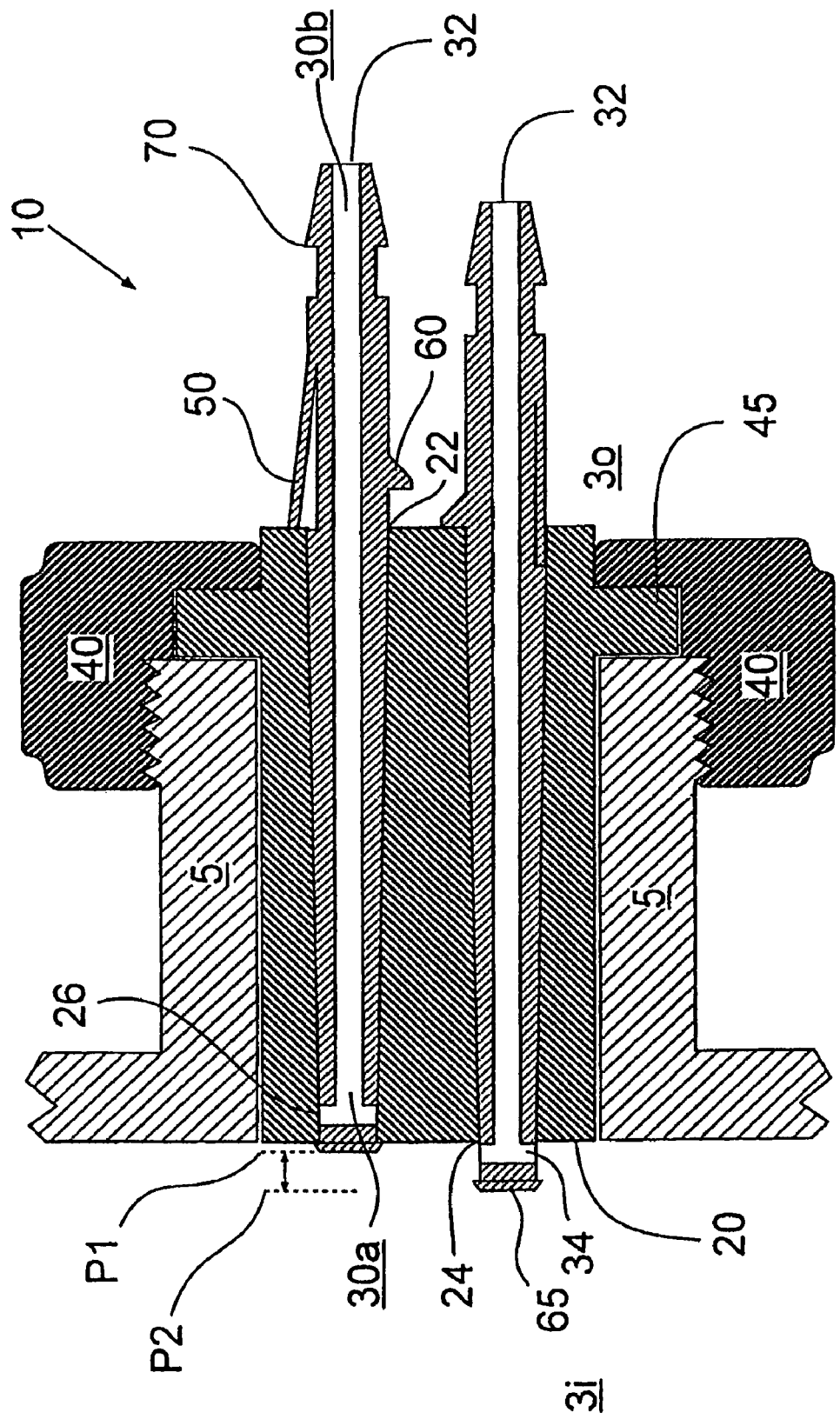
FIG. 2 schematically illustrates a particular embodiment of a port insert 10 suitable for incorporation, for example, into the fluid sampling device 100 shown in FIG. 1.

Although subject to several and diverse configuration, a preferred embodiment of the port insert is shown in FIG. 2. The port insert 10 therein comprises a monolithic body 20 and a plurality of elongate members 30. The body 20—preferably made of a monolithic elastomeric material—is provided with shafts 26 therethrough connecting first open ends 24 with a second open ends 22. The body is shaped to fit substantially water-tight within the host receptacle's port 5—much like a cork or plug or stopper—and such that the first open ends 24 are facing inside the fluid receptacle $3_i$, with the second open ends 22 facing outside the fluid receptacle $3_o$.

In respect of materials and methods, the body 20 of the port insert 10 will generally be formed monolithically (i.e., as a single, homogenous, unitary, unassembled piece) from polymeric material, for example, by well-known injection molding or like processes.

Examples of suitable polymeric material include, but are not limited to, polycarbonates, polyesters, nylons, PTFE resins and other fluoropolymers, acrylic and methacrylic resins and copolymers, polysulphones, polyethersulphones, polyaryl-sulphones, polystryenes, polyvinyl chlorides, chlorinated polyvinyl chlorides, ABS and its alloys and blends, polyurethanes, thermoset polymers, polyolefins (e.g., low density polyethylene, high density polyethylene, and ultra-high molecular weight polyethylene and copolymers thereof, polypropylene and copolymers thereof, and metallocene generated polyolefins.

The body 20 should be formed in consideration of conditions likely to be encountered in the course of in situ steam sterilization. The temperature and pressure of such sterilization is typically about 121° C. and 1 bar above atmospheric pressure. The use of temperatures and pressures up to and in excess of 142° C. and 3 bars is not too uncommon.

To accommodate easy installation of the fluid sampling device into the host receptacles, the port insert should be substantially cylindrical in shape and have an external diameter of about 0.985 inch (2.5 cm.) In the biopharmaceutical field, such configuration will allow the fluid sampling device 10 to be installed, without further custom engineering, into several commercially-available types of bioreactors, that already contain ports (e.g., so-called "Ingold Ports") of such dimensions, and which are currently used for probes and other sensors.

Each of the elongate members 30 are monolithic and rigid, and has a front $30_A$ and a back $30_B$. They are shaped to fit substantially water-tight within said shaft 26 such that the front thereof $30_A$ is proximate the first open end 24 and the back thereof $30_B$ is proximate the second open end 22. Each elongate member 30 is movable within said shaft 26 from a closed position $P_1$ to an open position $P_2$, such that the release of fluid out of said fluid receptacle through said port insert 10 is frustrated when the elongate member 30 occupies the closed position $P_1$ and enabled when the elongate member 30 occupies the open position $P_2$.

In a desirable embodiment, four elongate members, each having a length equal to or slightly greater than 1.600 inch (4.064 cm), are provided on the port insert 10. As shown in FIG. 2, each elongate member 30 is preferably configured as a hollow tube with a fluid passage way running substantially the entire length front $30_A$ to back $30_B$, culminating in openings 34 and 32 on both ends of the member. The opening(s) 34 on the front end $30_A$ are "uncovered" or otherwise made accessible to fluid only when the elongate member is moved into its "open" position $P_2$.

Although port insert 10 is structured to fit snugly within host port, to prevent it from being popped into or out of the port during use, additional mechanical restraints are highly desirable. In the embodiment shown in FIG. 2, the mechanical restraint is a threaded collar 40 that engages with and holds a port attachment portion 45, for example, an annular lip provided on the port insert when said collar 40 is screwed into port 5. In the embodiment shown in FIG. 3F, the mechanical restraint by which the port insert 10 is secured to the host port is a clamp 40F that engages with and holds a port attachment portion 45, for example, an annular lip, provided on the port insert when said clamp 40F is clamped onto port 5. Other mechanical restraints—such as screws, bolts, or mated interlocking parts—are known in the art. The mechanical restraints are preferably temporary mechanical devices that allow easy removal and disposal of spent devices.

As an alternative to a sample gating means comprising multiple elongate members, the present invention also contemplates a port insert comprising a single displaceable member that, by itself, functions to selectively and individually "open" and "close" each shaft provided in the port insert. A representative example of such sample gating means is presented in FIG. 3.

Figure 3:
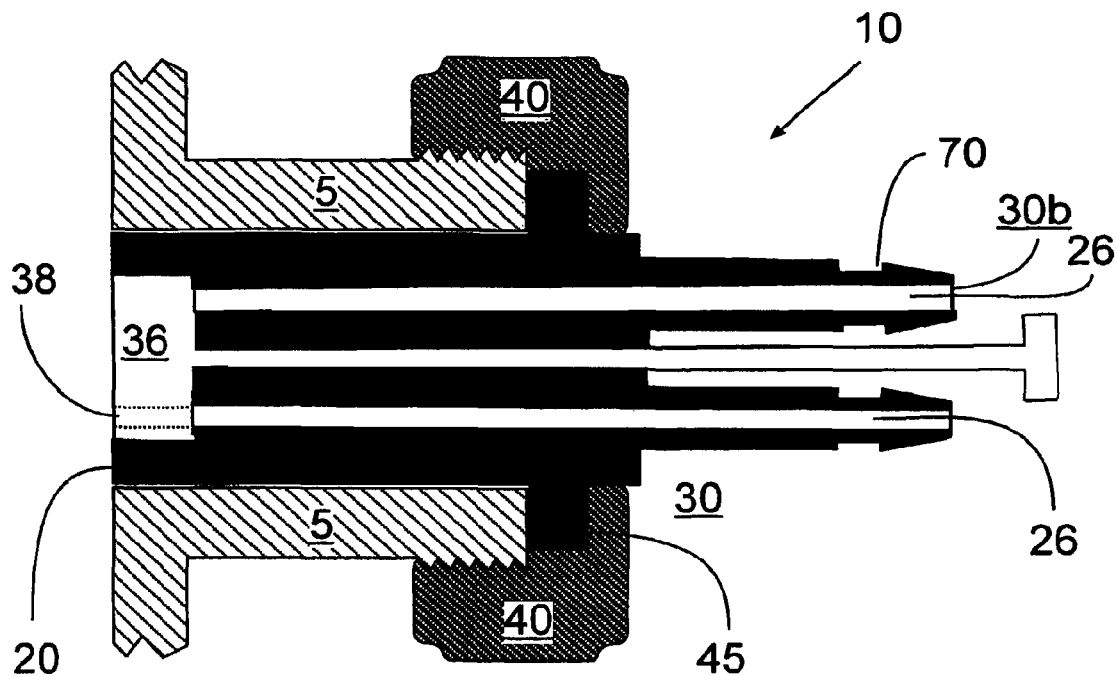
FIGS. 3, 3A, 3B, 3C, 3D 3E, and 3F schematically illustrate another particular embodiment of a port insert 10 suitable for incorporation, for example, into the fluid sampling device shown in FIG. 1.

In FIG. 3, the alternative port 10 comprises (a) a body 20 having a plurality of shafts 26 therethrough and (b) a rotatably displaceable member 36. Rotatably displaceable member 36 is provided with a passage 38 which can be selectively rotated into alignment with any of the shaft openings 24a, 24b, 24c, and 24d disposed on body 20. When the passage 38 and an opening are aligned, fluid sample can flow through the port insert 10 through the respectively selected shaft.

In practice—in contrast to the schematic nature of FIG. 3—both the passage 38 and member 36 should be structurally configured to optimize fluid flow, for example, by streamlining these parts to minimize so-called "dead spaces". Such configurations will vary among different applications. Regardless, suitable flow optimizing strategies are well known in the art.

The rotatably displaceable member 36 can be rotated by means of an integrated handle (shown in FIGS. 3, 3A, 3B, 3C, 3D, 3E, and 3F) that extends through and past the body 20. Where appropriate, the handle should extend sufficiently far from the body 20 to provide sufficient clearance for conduits to be connected to barbs 70, and thereby discourage potential restriction to flow resultant of pinching and/or extreme bending of the conduits.

As an alternative to an integrated handle, one can also employ a separate tool (e.g., an allen wrench 37 or screwdriver 39) to turn the rotatably displaceable member 36. For such instance, the rotatably displaceable member is configured with an appropriate tool engaging structure (e.g., slots, nuts, bolts, etc.).

Preferably, the rotatably displaceable member 36 should be capable of rotation in a single direction only, i.e., either clockwise or counter-clockwise, and such that alignment in any of the achievable "closed" or "open" positions, respective of said shafts, are definitively and discretely defined. Means should also be provided to prevent the member 36 from being rotated back into alignment with any spent shafts.

Figures 3A, 3B:
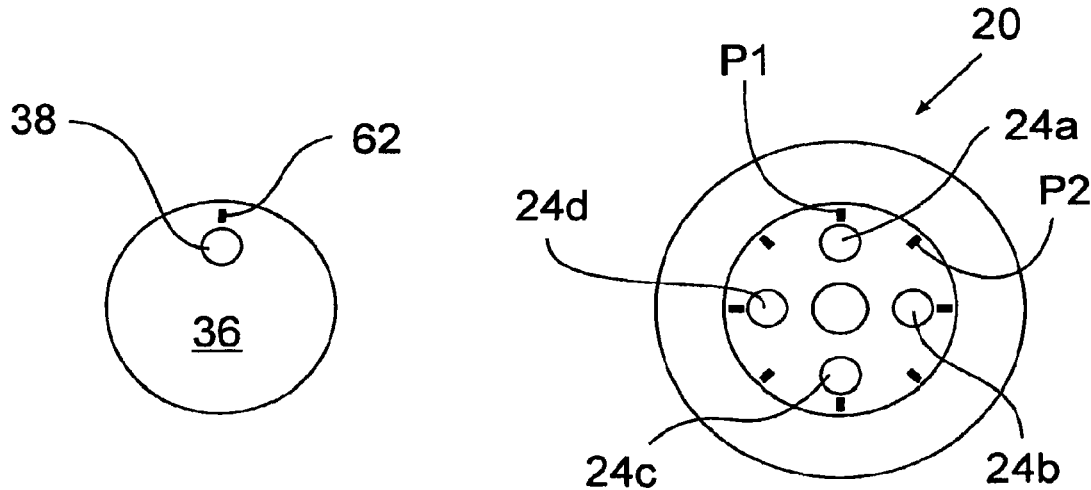
Figure 3C:
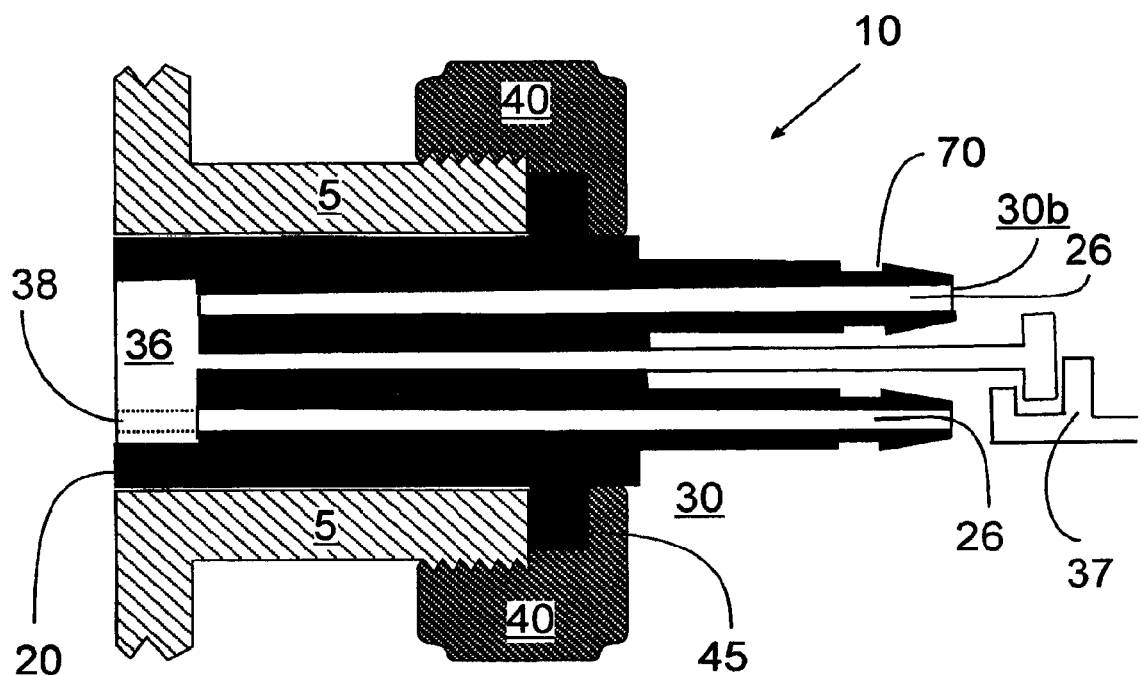
Figure 3D:
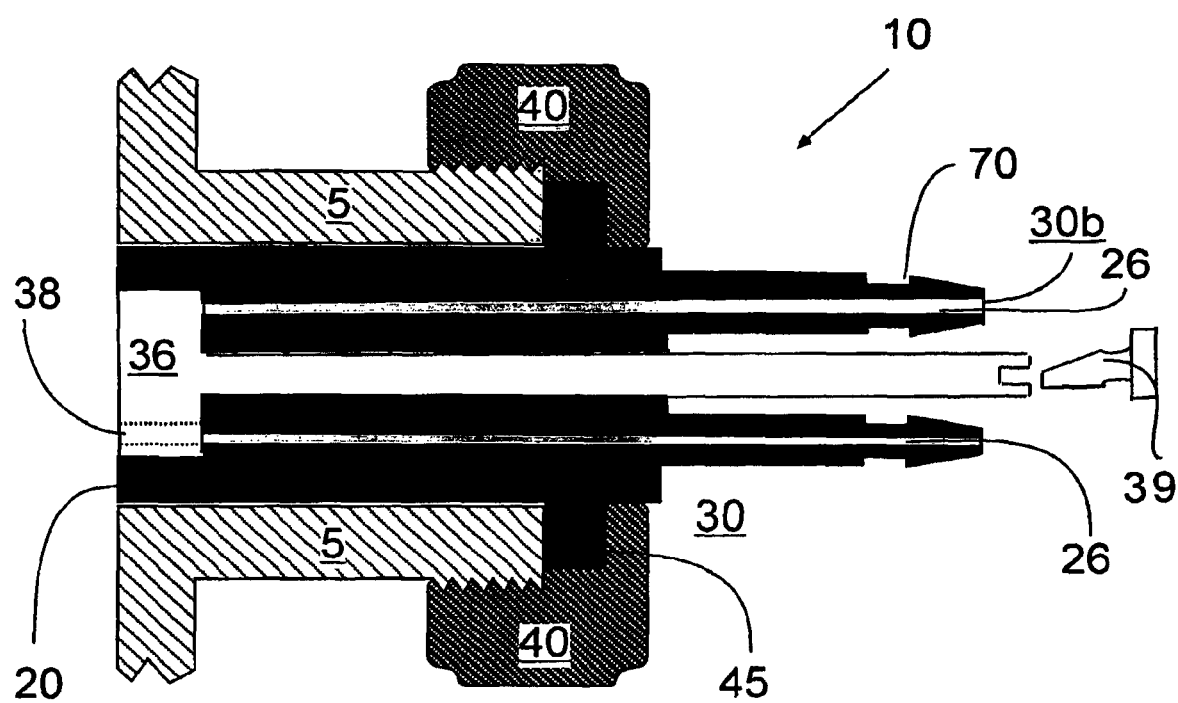
Figure 3E:
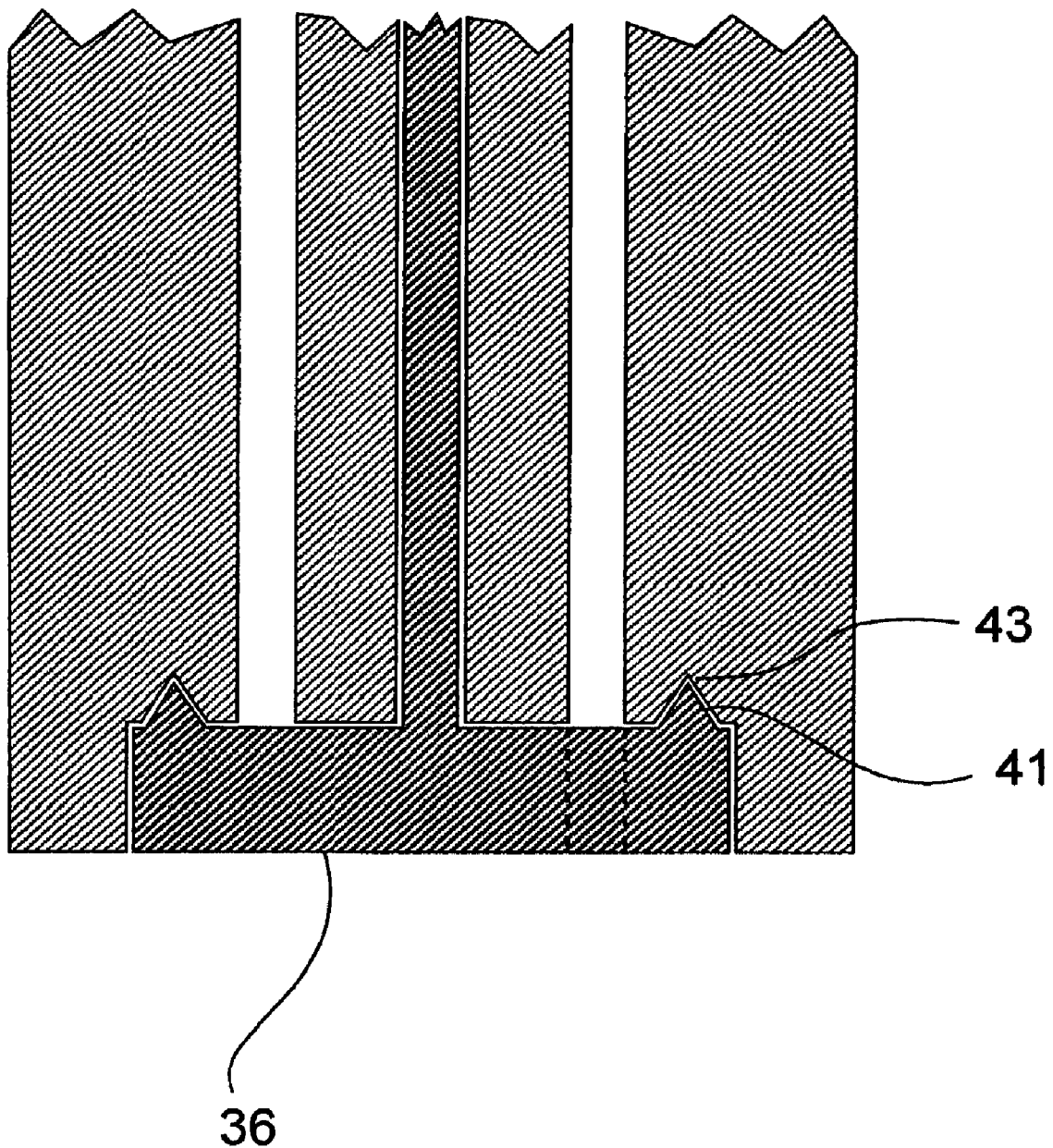
Figure 3F:
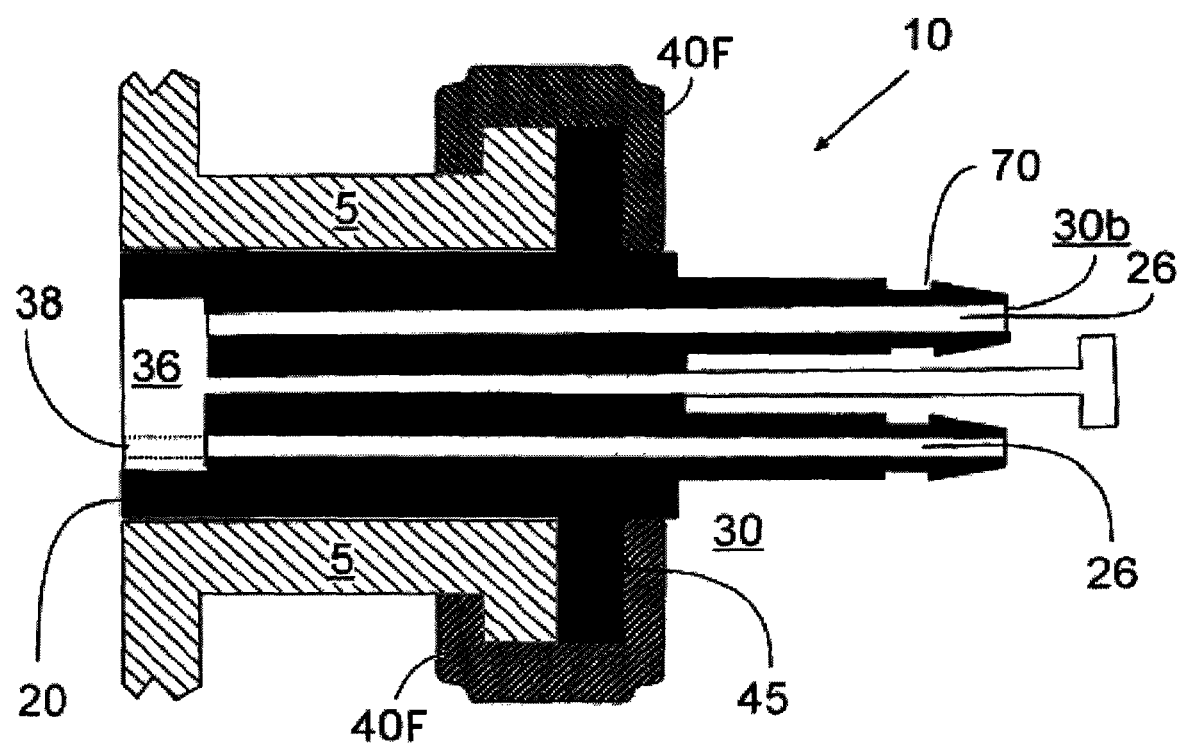

As shown schematically, in FIGS. 3A and 3B, discrete positions can be defined by using corresponding interlocking structures 62 and P1lP2 provided respectively on rotatably displaceable member 36 and monolithic body 20. When structure 62 (e.g., a tab) is engaged with structure PI (e.g., a slot), passage 38 is aligned definitively with opening 24a. Thus, the shaft 26 corresponding to opening 24a is "open" and "active", and the shafts corresponding to openings 24b, 24c1 and 24d1are "closed" and "inactive". After the desired volume of sample fluid has flown through the "active" shaft, it is then closed by rotating the member 36 such that structure 62 engages with structure P2 (e.g., another slot). In this position, passage 38 is not aligned with any of openings 24a, 24b, 24c, and 24d1 and thus, all shafts correspondent therewith are "closed" and "inactive". When desired, the remaining unused shafts can be "opened" and "closed" sequentially in the same manner. Those skilled in the art will know of suitable configurations (e.g., such as a ratchet-like configuration 41,43 as shown in FIG. 3E) that can render member 26 rotatable in one direction only, as well as prevent it from being rotated more than one time around (e.g., a brake or other physical obstruction).

To further assist manual rotation and alignment, graphical, textual, or otherwise informative indicia or structures (e.g., a pointer in combination with symbolic icons) can be integrated into or otherwise provided on, for example, the handle, the body 20, or both, to inform a user of the current position of rotatably displaceable member 36. Likewise, the interlocking structures (e.g., 62, P1, and P2) can also be configured to provide an audible (e.g., clicking) or frictional (e.g., variable resistance) clue to a user during rotation indicative of the displacement and/or position of the rotatably displaceable member 36.

As mentioned, the sample containers used for the present invention are preferably flexible bags, particularly so when the fluid sampling device is intended for use in biopharmaceutical applications or like applications that have comparatively high aseptic requirements. Unlike many conventional sampling devices, the fluid sampling device 100 of the present invention does not rely on valves, pumps, and like extrinsic mechanisms to promote, urge, facilitate, or otherwise affect the flow of sample liquid out of the host fluid receptacle 5 into an available sample container 130. Rather, fluid flows through the aseptically-isolated flow path of the device 100 by a combination of ambient gravitational forces and the extant pressurization of the host fluid receptacle. Initially provided in a collapsed or partially-collapsed state, the flexible bag (or functionally-equivalent expansible fluid container) expands, decompresses, or otherwise "fills-out" as withdrawn sample fluid flows thereinto.

Although the use of a flexible, bag-like sample container 130 is preferred, a rigid sample container can also be used without departing from objectives of the present invention. For example, the sample container can be configured as a spacious, rigid box, bulb, vial, or bottle. A vent—preferably of modest construction—can be provided to permit the displacement of contained gas as sample fluid flows thereinto.

One type of vent (not shown) that can be implemented with little cost, yet still provide good aseptic functionality, is constructed by "patching" and opening the rigid container (i.e., above the expected fluid fill level thereof with a gas permeable sheet of fluoropolymer membrane (e.g., "Gore-Tex"—brand membrane available from W.L. Gore and Associates of Wilmington, Del.) or a substantially gas permeable sheet of polyethylene fiber (e.g., "Tyvek"-brand material available from E.I. du Pont de Nemours, Inc. of Wilmington, Del.).

As an alternative to complete rigidity, it is envisioned that a sample container comprise rigid side walls that bend and flex along folds or creases or crumple zones, and the like, such that the sample container is capable of collapsing or otherwise diminishing its volume. Examples of collapsible rigid configurations include accordion-like configurations, bellows-like configurations, and other configurations having pleated side walls.

The mechanisms underlying the operation of the fluid sampling device 100 call for a certain rigidity in the configuration of elongate members 30. Aside from durability, the rigidity allows the members to be pushed through the shaft into their open positions with sufficient and appropriate force to overcome the frictional forces that create the liquid tight seal, without the elongate member flexing, bending, crumpling, or otherwise deforming, such circumstances potentially leading to sampling failures, and/or more catastrophically, breach of extant sterile conditions.

Because several rigid members 30 are provided through the port insert 10, physical space immediately outside the insert will likely be cramped, and may not accommodate sample containers large enough to collect the volumes of fluid desired. Hence, the sample containers are placed further geographically downstream of the elongate members 130, with lengths of flexible conduit material 120 provided therebetween.

Although a flexible conduit and a flexible bag-like sample container can be formed as one component, in all likelihood, the conduits 120 and elongate members 30—owing to their differing preferred material composition—are formed separately and later assembled. For example, in one embodiment, conduits 120 are made of flexible elastomeric material, whereas elongate members 30 are made of high-impact, rigid polymeric material. In such and like instances, the back end 30$_B$ of each rigid elongate member 30 can be provided with means for securely attaching the flexible conduit, such as the barbed end 70 shown in FIG. 2.

In the preferred configuration, means should be provided to prevent the elongate means from being prematurely moved into its open position, as well as prevent it from being moved too far past its open and/or closed positions. While such means will vary depending on the ultimate configuration of the fluid sampling device, the embodiment represented in FIG. 2 illustrates certain examples thereof. For example, anchor 50 is provided to prevent the elongate member 30 from being pushed into its open position $P_2$ prematurely. When sampling is commenced, the anchor 50 can be moved into a position in which it no longer impedes the transit of the member 30 through the shaft. When pushed in, block 60 prevents the member from being pushed in too far. A cap 65 can also be provided on the front 30$_A$ of member 30 to—in addition to creating a liquid tight seal—prevent the member 30 from being pulled out.

For applications having comparatively strict sterility requirements (e.g., biopharmaceutical applications), the present invention is preferably embodied in kit form, comprising, enclosed within sterile packaging, the following principal kit contents: (a) a pre-sterilized port insert constructed in accordance with any embodiment described and/or otherwise enabled herein; (b) a supply of pre-sterilized flexible tubing, preferably "pre-cut to length", connected or connectable to the elongate members of said port insert; and (c) a supply of pre-sterilized sample containers connected or connectable to said flexible tubing, the pre-sterilized sample containers also constructed in accordance with any embodiment described and/or otherwise enabled herein. It is preferred that the kit be pre-assembled and then sterilized in its bag or container, using well known means such as gamma radiation, ethylene oxide gas, and the like.

The provision of the present invention in kit form advances certain objectives either not possible or difficult to accomplish otherwise. Foremost, the kit assures that all its contents are pre-sterilized, and essentially remain so until use. Further, ease of installation, assembly, and operation are improved since all kit contents are pre-selected, pre-sized, and pre-matched to assure proper fit and assembly. And, along similar lines, a kit-based approach promotes standardization of the kit's contents, as well as their manufacture and packaging, leading to reduced product costs, fostering the product's "disposability", and broadening the accessibility of the technology to the public.

Optionally, the kit may also contain, for example, means for locking the port insert within the port provided on a host fluid receptacle (e.g., collar 40); accessories and other means used for assembling the fluid sampling device (e.g., clamps, connectors, junctions, manifolds, and the like); means for mounting, fixing, and/or positioning the assembled fluid sampling device relative to the host receptacle (e.g., adhesive strips, fasteners, brackets, and the like); and a disposal bag for disposing a spent fluid sampling device. These and other optional kit contents, if included, are all sterilized in their packaging. Both the principal and optional kit contents can be provided, if desired, individually or collectively wrapped (i.e., in groups) within said sterile packaging, thus providing additional sterile barriers.

Although certain embodiments of the invention are disclosed, those skilled in the art, having the benefit of the teaching of the present invention set forth herein, can affect numerous modifications thereto. These modifications are to be construed as encompassed within the scope of the present invention as set forth in the appended claims.

What is claimed is:

1. A fluid sampling device, comprising:
   a first member having a front side, a back side, and a plurality of shafts, each of said plurality of shafts having an inlet opening arranged at the front side and an outlet opening arranged at the back side for fluid to flow therethrough, the outlet opening being configured to attach a flexible conduit thereto; and
   a second member having a passage extending from a first side to a second side of the second member for fluid to flow there-through;
   wherein said first member and said second member are rotatable with respect to each other such that each of said plurality of shafts of said first member can be sequentially aligned with said passage of said second member, and the alignment being such that fluid can flow through the first member only through a single shaft at one time, the single shaft being the shaft that is aligned with said passage of said second member.

2. The fluid sampling device of claim 1, wherein said first member and said second member are concentric with respect to each other.

3. The fluid sampling device of claim 1, wherein said plurality of shafts comprises four shafts.

4. The fluid sampling device of claim 1, further comprising a port attachment portion on said first member.

5. The fluid sampling device of claim 4, further comprising a mechanical restraint operable to attach said port attachment portion to a port of a fluid container.

6. The fluid sampling device of claim 5, wherein said mechanical restraint is a clamp.

7. The fluid sampling device of claim 1, further comprising an interlocking structure for interlocking said first member and said second member with respect to each other.

8. The fluid sampling device of claim 7, wherein said interlocking structure comprises a ratchet-like configuration.

9. The fluid sampling device of claim 7, wherein said interlocking structure comprises a ratchet configuration.

10. The fluid sampling device of claim 7, wherein said interlocking structure comprises at least one tab and at least one slot.

11. The fluid sampling device of claim 10, wherein said at least one tab is on said second member.

12. A fluid sampling device, comprising:
a first member having a plurality of openings, each of said openings being arranged substantially parallel to each other and extending axially through said first member; and
a second member having a passage extending from a first side to a second side of the second member, wherein said passage of said second member is arranged at least partially inside a cavity of said first member and wherein said first member and said second member are rotatable with respect to each other such that said fluid sampling device is operable to sequentially align each of said openings of said first member with said passage of said second member, and the alignment being such that fluid can flow through the first member only through a single opening at one time, the single opening being the opening that is aligned with said passage of said second member,
further comprising a port attachment portion on said first member and a mechanical restraint operable to attach said port attachment portion to a port of a fluid container wherein said mechanical restraint is a clamp.

13. A fluid sampling device, comprising:
a first member having a plurality of openings, each of said openings being arranged substantially parallel to each other and extending axially through said first member; and
a second member having a passage extending from a first side to a second side of the second member, wherein said passage of said second member is arranged at least partially inside a cavity of said first member and wherein said first member and said second member are rotatable with respect to each other such that said fluid sampling device is operable to sequentially align each of said openings of said first member with said passage of said second member, and the alignment being such that fluid can flow through the first member only through a single opening at one time, the single opening being the opening that is aligned with said passage of said second member,
further comprising an interlocking structure for interlocking said first member and said second member with respect to each other wherein said interlocking structure comprises a ratchet-like configuration.

14. A fluid sampling device, comprising:
a first member having a plurality of openings, each of said openings being arranged substantially parallel to each other and extending axially through said first member; and
a second member having a passage extending from a first side to a second side of the second member, wherein said passage of said second member is arranged at least partially inside a cavity of said first member and wherein said first member and said second member are rotatable with respect to each other such that said fluid sampling device is operable to sequentially align each of said openings of said first member with said passage of said second member, and the alignment being such that fluid can flow through the first member only through a single opening at one time, the single opening being the opening that is aligned with said passage of said second member,
further comprising an interlocking structure for interlocking said first member and said second member with respect to each other wherein said interlocking structure comprises a ratchet configuration.

15. A fluid sampling kit, comprising:
a first member having, a front side, a back side, and a plurality of shafts, each of said plurality of shafts having an inlet opening arranged at the front side and an outlet opening arranged at the back side for fluid to flow there-through; and
a second member having a passage for fluid to flow there-through, wherein said first member and said second member are rotatable with respect to each other such that, in use, each of said plurality of shafts of said first member can be sequentially aligned with said passage of said second member;
a plurality of flexible conduits attachable to an end of each of said plurality of shafts of said first member; and
a plurality of sample containers attachable to an end of each of said flexible conduits.

16. The fluid sampling kit of claim 15, wherein at least one of said plurality of sample containers includes a vent.

17. The fluid sampling kit of claim 15, wherein said first member and said second member are concentric with respect to each other.

18. The fluid sampling kit of claim 15, wherein said plurality of shafts comprises four shafts.

19. The fluid sampling kit of claim 15, further comprising a port attachment portion.

20. The fluid sampling kit of claim 19, further comprising a mechanical restraint operable to attach said port attachment portion to a port of a fluid container.

21. The fluid sampling kit of claim 20, wherein said mechanical restraint is a clamp.

22. The fluid sampling kit of claim 15, further comprising an interlocking structure for interlocking said first member and said second member with respect to each other.

23. The fluid sampling kit of claim 22, wherein said interlocking structure comprises a ratchet-like configuration.

24. The fluid sampling kit of claim 22, wherein said interlocking structure comprises a ratchet configuration.

25. The fluid sampling kit of claim 22, wherein said interlocking structure comprises at least one tab and at least one slot.

26. The fluid sampling kit of claim 25, wherein said at least one tab is on said second member.

27. A method for operating a fluid sampling device in an aseptic manner, comprising:
providing a fluid sampling device having a first member having a front side, a back side, and a plurality of shafts, each of said plurality of shafts having an inlet opening arranged at the front side and an outlet opening arranged at the back side for fluid to flow there-through, and a second member having a passage for fluid to flow there-through;
installing said fluid sampling device to a port of a fluid container;

attaching a first flexible conduit to the outlet opening of a first of said plurality of shafts and attaching a second flexible conduit to the outlet opening of a second of said plurality of shafts;

rotating said first member and said second member with respect to each other such that the first of said plurality of shafts of said first member is aligned with said passage of said second member;

sampling fluid from said fluid container through said first of said plurality of shafts in an aseptic manner;

rotating said first member and said second member with respect to each other such that the second of said plurality of shafts of said first member is aligned with said passage of said second member; and sampling fluid from said fluid container through said second of said plurality of shafts in an aseptic manner.

28. The method of claim 27, further comprising installing flexible conduits onto an end of each of said plurality of shafts.

29. The method of claim 28, further comprising installing a sample container onto an end of each of said flexible conduits.

30. The method of claim 29, wherein said sampling fluid from said fluid container comprises sampling fluid to said sample container.

31. The method of claim 27, further comprising rotating said first member and said second member with respect to each other such that said first of said plurality of shafts of said first member and said passage of said second member are no longer aligned with each other, thereby closing said first of said plurality of shafts.

32. The method of claim 27, wherein said first member and said second member are rotatable with respect to each other such that each of said plurality of shafts of said first member can be sequentially aligned with said passage of said second member, and such that fluid can flow through no more than one of said plurality of shafts at one time.

* * * * *